United States Patent [19]
Ralston et al.

[11] Patent Number: 5,922,542
[45] Date of Patent: Jul. 13, 1999

[54] DIAGNOSIS OF PREDISPOSITION TO OSTEOPOROSIS

[75] Inventors: Stuart Hamilton Ralston, Aberdeen, United Kingdom; Struan Frederick Airth Grant, Sydney, Australia

[73] Assignee: Gemini International Holdings Limited, Monaco

[21] Appl. No.: 08/808,158

[22] Filed: Feb. 28, 1997

[30] Foreign Application Priority Data

Feb. 29, 1996 [GB] United Kingdom .................... 9604305

[51] Int. Cl.$^6$ .............................. C12Q 1/68; C07H 21/04; C12P 19/34
[52] U.S. Cl. .............................. 435/6; 435/91.2; 435/810; 536/23.5; 536/24.31; 536/24.33; 935/8; 935/78
[58] Field of Search .............................. 435/6, 91.2, 810; 536/23.5, 24.31, 24.33; 935/8, 78

[56] References Cited

U.S. PATENT DOCUMENTS 5,558,988  9/1996  Prockop ....................................... 435/6

FOREIGN PATENT DOCUMENTS

WO 93/11149  6/1993  WIPO.
WO 94/11532  5/1994  WIPO.

OTHER PUBLICATIONS

Willing et al. American Journal of Human Genetics (1994) 55: 638–647.

Jimenez et al, The Journal of Biological Chemistry (1994) 269: 12684–12691.

Bornstein, P. et al., "Regulatory elements in the first intron contribute to transcriptional control of the human α1(I) collagen gene," *Proc. Natl. Acad. Sci. USA* 84:8869–8873 (1987).

D'Alessio, M. et al., "Complete nucleotide sequence of the region encompassing the first twenty-five exons of the human proα1(I) collagen gene (COL1A1)," *Gene* 67:105–115 (1988).

Grant, S.F.A. et al., "Reduced bone density and osteoporosis associated with a polymorphic Sp1 binding site in the collagen type I α 1 gene," *Nature Genetics* 14(2):203–205 (Oct. 1996).

Ralston, S.H., "Genetic markers of bone metabolism and bone disease," *Scand. J. Clin. Lab. Invest.* 57(Suppl. 227):114–121 (1997).

Rossouw, C.M.S. et al., "DNA Sequences in the First Intron of the Human Pro–α1(I) Collagen Gene Enhanced Transcription," *J. Biol. Chem.* 262(31):15151–15157 (1987).

Spotila, L.D. et al., "Mutation in a gene for type I procollagen (COL1A2) in a woman with postmenopausal osteoporosis: Evidence for phenotypic and genotypic overlap with mild osteogenesis imperfecta," *Proc. Natl. Acad. Sci. USA* 88:5423–5427 (1991).

Spotila, L.D. et al., "Mutation Analysis of Coding Sequences for Type I Procollagen in Individuals with Low Bone Density," *J. Bone Min. Res.* 9(6):923–932 (1994).

Sykes, B., "Bone disease cracks genetics," *Nature* 348:18–20 (1990).

*Primary Examiner*—Carla J. Myers
*Attorney, Agent, or Firm*—Sterne, Kessler, Goldstein & Fox P.L.L.C.

[57] ABSTRACT

Diagnostic means that determines the genotype of a collagen gene of an individual is described. A polymorphism in the collagen gene correlates with predisposition to osteoporosis, so diagnosis of a predisposition is achieved using the diagnostic means. An isolated gene comprising the nucleotide substitution of the polymorphism is also described, as is a method of diagnosis based on the presence or absence of the polymorphism.

10 Claims, 4 Drawing Sheets

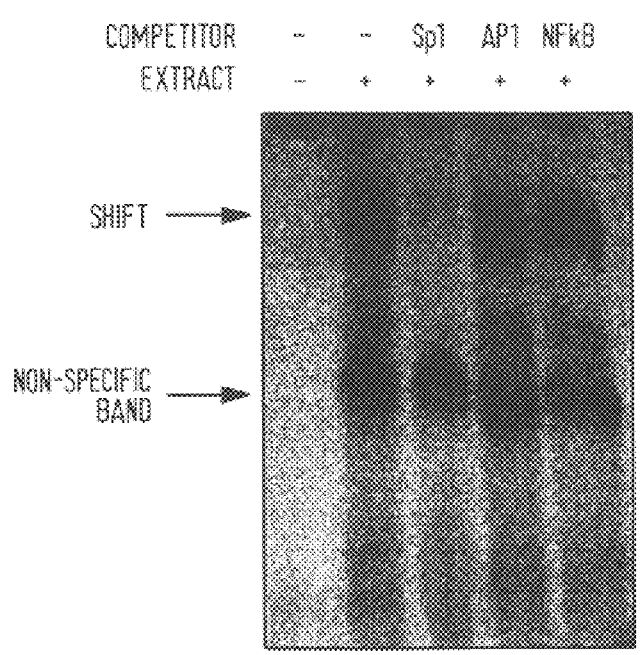
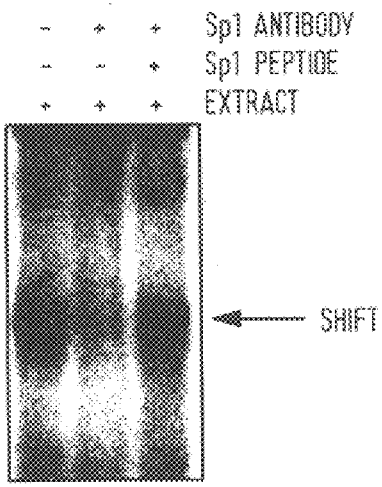

DIAGNOSIS OF PREDISPOSITION TO OSTEOPOROSIS

BACKGROUND OF THE INVENTION

1. Field of the Invention

This invention relates to diagnostic method and apparatus based upon a polymorphism in a collagen gene. More specifically, this invention relates to method and apparatus for diagnosis of pre-disposition to certain disease states, by screening for the presence of this polymorphism, and more specifically to diagnosis of predisposition to osteoporosis. The invention further relates to a collagen gene containing the polymorphism.

2. Related Art

Hormone replacement therapy is an established treatment for osteoporosis and has proved successful in halting further decline in bone density that is characteristic in women suffering from this disease. Hormone replacement therapy is generally not, however, able to bring about a reversal of osteoporosis, that is to say it is not capable of inducing an increase in the bone density of sufferers.

It would, accordingly, be of particular advantage to be able to identify with increased accuracy those individuals having a predisposition or increased susceptibility to osteoporosis. Suitable therapy could then be put into place before the effects of osteoporosis set in.

SUMMARY OF THE INVENTION

It is an object of this invention to provide method and apparatus for detecting individuals having a predisposition or susceptibility to certain disease states, in particular, osteoporosis. It is a further object of the invention to identify individuals having such a predisposition or susceptibility by identifying those individuals with an altered collagen gene. It is another object of the invention to provide a therapy for those individuals have a predisposition or susceptibility to certain disease states. A still further object of the invention is to provide a therapy for those individuals having a predisposition or susceptibility to osteoporosis.

BRIEF DESCRIPTION OF THE FIGURES

FIGS. 1A and 1B are photographs of gels which show a polymorphism in intron 1 of the COLIA1 gene at an Sp1 binding site. FIG. 1A: EMSA assay was performed with labeled double stranded oligonucleotides encompassing putative polymorphic Sp1 site in the COLIA1 first intron as probe. The band shift (arrowed) was abolished by excess cold Sp1 oligo whereas the AP1 and NFkB oligos had no effect, consistent with the presence of an Sp1 site. The position of a non-specific band is indicated. FIG. 1B shows the effect of an Sp1-specific monoclonal antibody (0.5 mg) on the band shift shown in FIG. 1A. The Sp1 antibody attenuated the shift and this effect was abrogated by co-incubation with an excess of Sp1 peptide (0.5 mg), confirming specificity for Sp1 binding;

FIG. 3A: Adjusted BMD values in the spine and FIG. 3B: adjusted BMD values at the hip are related to menopausal age and COLIA1 genotype. BMD data for "Ss" and "Ss" groups were combined in view of the small number of "ss" individuals (4 perimenopausal and 5 late postmenopausal) and because BMD values were similar in these subgroups. Although the difference in BMD between genotypes was small in pre-menopausal and early post-menopausal women (0–5 yrs), there was a significant difference in spine BMD in late postmenopausal women (>5 yrs). A similar trend was observed for hip BMD, but this just failed to reach significance (p=0.06).

DETAILED DESCRIPTION OF THE PREFERRED EMBODIMENTS

Figure 2:
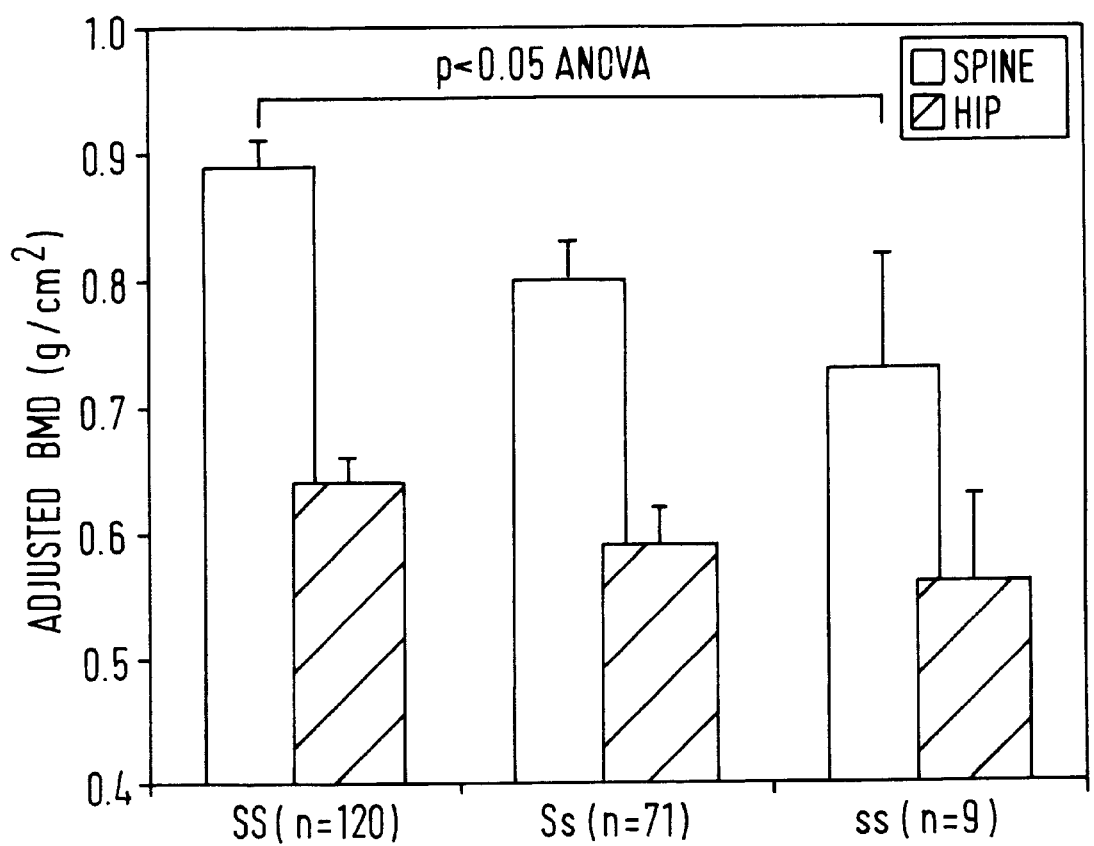
FIG. 2 shows a polymorphic Sp1 site in the COLIA1 gene is related to bone mineral density. Adjusted BMD values at the spine were significantly related to COLIA1 genotype with evidence of a gene-dose effect. A similar (but non-significant) trend was seen for BMD at the femoral neck (hip). The difference between spine BMD values in "SS" and "Ss" groups was significant (p<0.02) as was the difference between "SS" and the "Ss" "ss" groups combined (p<0.02).

Accordingly, a first aspect of the invention provides a method of diagnosis comprising determining whether an individual is homozygous or heterozygous for a collagen gene and a polymorphism thereof. In an embodiment of the invention, the method of diagnosis is to screen for an individual at risk of a condition or disease correlated with presence of the polymorphism.

In an embodiment of the invention, described in detail hereafter, the diagnosis employs polymerase chain reaction or single strand conformational polymorphism assay, or both, and determines whether an individual possesses a wild type collagen gene or a polymorphism thereof. Each individual may be homozygous for the wild type, heterozygous for the wild type and a polymorphism, or homozygous for polymorphisms in the collagen gene. Presence of a polymorphism correlates with predisposition to osteoporosis.

In a particular embodiment of the invention, the polymorphism is located in a transcriptional control region of a collagen gene, and the method of the invention comprises analyzing the transcriptional control region to screen for a polymorphism therein. The method further comprises use of an indicator means to react to the presence of the polymorphism.

Indicator means typically induces a detectable signal upon presence of the polymorphism, and can induce a color change or a coagulation or induce a restriction site, detectable by further analytical steps. Another indicator means comprises an antibody that has binding affinity that distinguishes between a wild type sequence and a polymorphism.

A particular method of the invention comprises screening for a polymorphism in a binding site for Sp1, a nuclear binding protein, wherein presence of the polymorphism correlates with predisposition to osteoporosis.

In use of a specific embodiment of the invention to be described below in further detail, an individual is screened to determine whether he or she possess an Sp1 binding site in a collagen gene which is a published sequence or is a polymorphism thereof in which a guanosine nucleotide at position 1245 has been replaced by an thymidine nucleotide. In this specific embodiment, the presence of the polymorphism in which guanosine is replaced by thymidine at position 1245 correlates with a predisposition to osteoporosis.

Screening is carried out, for example, using PCR primers adapted to amplify a portion of the Sp1 binding site that includes the nucleotide at position 1245. It is preferred that the PCR primers are selected so as to amplify a region of the gene that surrounds position 1245 and includes at least six nucleotides on either side of this position. PCR techniques are well known in the art and it would be within the ambit of a person of ordinary skill in this art to identify primers for amplifying a suitable section of the Sp1 binding site including position 1245. PCR techniques are described for example in EP-A-0200362, EP-A-0201184, and U.S. Pat. Nos. 4,683,195, 4,683,202 and 4,965,188.

In a further embodiment of the invention, the diagnostic method comprises analysis of the Sp1 binding site on the collagen gene using single strand conformational polymorphism (SSCP) mapping. It is preferred that the PCR primers for this purpose are selected so as to be homologous with a region of the genome within 200 bp of position 1245 on the collagen gene. It is further preferred that the PCR primers are selected so that position 1245 is substantially towards the middle of the amplified DNA segment.

A second aspect of the invention provides diagnostic means adapted to determine genotype of a collagen gene; thus, the diagnostic means diagnoses presence of a polymorphism in a collagen gene. The diagnostic means preferably comprises PCR primers adapted to amplify a region of a transcriptional control region in a collagen gene, preferably a DNA segment comprising a nucleotide at position 1245 on a Sp1 binding site on a collagen gene. It is preferred that the PCR primers are adapted to amplify a DNA segment that is up to 1 kb in length, more preferably up to 500 bp in length. In a particular embodiment of the invention the segment is approximately 260 bp in length.

Optionally, the diagnostic means further comprises means to determine which nucleotide is found at position 1245 at an Sp1 binding site on the collagen gene. An example is a restriction endonuclease capable of cleaving the gene only if the polymorphism is present, alternatively, capable of cleaving only the gene, or a normal variant thereof, in which the nucleotide at position 1245 is guanosine.

The invention further provides a diagnostic kit comprising diagnostic means according to the second aspect of the invention, optionally within a container. Thus, the invention further provides a diagnostic kit comprising a carrier means such as a carton or box being compartmentalized to receive in close confinement therein the diagnostic means according to the invention, optionally within a container means such as a vial, tube, ampule, and the like. Further container means may also be present which comprise other elements of the diagnostic assay as described herein.

A third aspect of the invention provides a collagen gene, or a fragment thereof, in which a guanosine nucleotide at position 1245 is replaced with an thymidine nucleotide. The fragment comprises position 1245 and is at least 30 nucleotides in length. Preferably, the gene is an isolated DNA molecule which means that it is free from other DNA molecules that are naturally associated therewith in nature.

The present invention is based upon the discovery of a single base polymorphism in an Sp1 binding site of a human collagen gene; there are 4 Sp1 binding sites in the first intron. A further aspect of the discovery is that the polymorphism is correlated with a predisposition to a osteoporosis. The invention is of advantage in that by screening for the presence of the polymorphism it is possible to identify individuals likely to have this genetic predisposition. Accordingly, a fourth aspect of the invention provides a method of therapy comprising screening an individual for a predisposition to osteoporosis and, if a genetic predisposition is identified, treating that individual to delay or reduce or prevent the osteoporosis. A suitable treatment to prevent or reduce or delay osteoporosis is hormone replacement therapy. The use of this therapy is well known in the art. According to the invention, hormone replacement therapy can thus be commenced in individuals likely to have a predisposition to osteoporosis but in whom osteoporosis has not yet begun to any significant extent. Another suitable treatment is use of bisphosphonates, and still further treatments will be known to a person of skill in the art.

It is known that the use of hormone replacement therapy can carry with it a concomitant increased risk of breast cancer. The invention offers the advantage that the increased risk of breast cancer associated with hormone replacement therapy can be accepted only by those women who are known to have a likelihood of predisposition to osteoporosis. In an embodiment of the fourth aspect of the invention, the predisposition of an individual to osteoporosis is assessed by determining whether that individual is homozygous for a collagen gene in which nucleotide 1245 is guanosine, is heterozygous for this gene and the polymorphism in which guanosine at position 1245 is replaced by thymidine, or is homozygous for the polymorphism.

According to the invention, an individual who is T/T homozygous for the polymorphism is classified as being at highest risk. An individual being G/T heterozygous is classified as having moderate risk. An individual being G/G homozygous is classified as being in the lowest risk category. Optionally, the assessment of an individual's risk factor is calculated by reference both to the presence of a collagen gene polymorphism and also to other known genetic or physiological or dietary or other indications. The invention in this way provides further information on which measurement of an individual's risk can be based.

A specific embodiment of the invention is the nucleotide sequence of SEQ ID NO: 1, listed in the sequence listing below. In SEQ ID NO: 1, the polymorphism lies in T in place of G at position 1245 on the gene sequence which is position 240 in SEQ ID NO: 1. For reference, this polymorphism at base 1245 in collagen gene sequence corresponds to base 1240 in the published sequence of Bornstein PNAS 1987;84:8869–8873.

Sp1 binding sites are at 1210–1219 and 1245–1254 in the collagen gene sequence. In addition, SEQ ID NO: 1 comprises 5 other consistent differences to that reported by Bornstein. Two additional polymorphisms (a T insertion at base +498 in Bornstein paper and a C-G substitution at base 811 in Bornstein paper) have also been found in our studies. These polymorphisms form further aspects of the invention.

In further specific embodiments of the invention, diagnostic means comprises primers SEQ ID NO:s 2 and 3, the sequences of which are shown in the sequence listing below. The 5' end of SEQ ID NO: 2 binds at position 1006. The 3' end of SEQ ID NO: 3 binds at position 1246. Preparation of further primers suitable for determining genotype of a collagen gene will be within the ambit of a person of ordinary skill in the art.

Osteoporosis is a common condition characterized by reduced bone mass, microarchitectural deterioration of bone tissue and increased fracture risk. The risk of osteoporotic fracture is related to bone mineral density, (BMD) which in turn, is under strong genetic control. Although the genes which regulate bone mass are incompletely defined, the collagen type I genes (COLIA1 and COLIA2) are important candidates, since mutations affecting their coding regions give rise to osteogenesis imperfecta (OI)—a rare disease characterized by severe osteoporosis and multiple fractures. Extensive DNA sequencing in osteoporotic individuals has however revealed no abnormality of the COLI coding regions.

In a specific embodiment of the invention described in detail below, PCR-SSCP is used to screen for a polymorphism in the transcriptional control region of COLIA1 to determine the presence of absence of a G/T polymorphism in the first intron at a recognition site for the nuclear binding protein Sp1—an important regulator of gene transcription.

Having now generally described the invention, the same will be more readily understood through reference to the following Examples which are provided by way of illustration, and are not intended to be limiting of the present invention, unless specified.

EXAMPLE 1

The study was based in a regional referral center for bone diseases which serves a white Caucasian population of about 0.5 million from a geographically isolated region in the UK. The study group comprised 200 women, 108 (54%) of whom were consecutive referrals for clinical evaluation; the remainder were drawn at random from the local population. Individuals with diseases known to affect bone metabolism (corticosteroid use, pituitary disease, immobilization, primary hyperparathyroidism, neoplasia, thyrotoxicosis) were excluded. The age range was 45–88 years, with a mean (+sem) age of 60.1+0.73 years. One hundred and seventy four women (87%) were post-menopausal with mean of 13.3+0.78 years elapsed since menopause (defined as the absence of menstruation for 6 months) 18.

According to World Health Organization (WHO) criteria, 22% of the study group were normal, 32% were osteopaenic and 46% were osteoporotic. These proportions are expected in a predominantly postmenopausal cohort of women, since the prevalence of osteoporosis increases with age. A subgroup of 55 individuals (27.5%) had vertebral compression fractures, diagnosed clinically and by the presence of one or more wedge or biconcave vertebral deformities on spinal radiographs.

Screening of the COLIA1 transcriptional control regions (promoter and first intron 20,21) by PCR-SSCP showed evidence of 3 polymorphisms, all of which were in the first intron; two of these were rare (allele frequency ~4% and ~3%) and one common (allele frequency ~22%). Since osteoporosis is a common disease, further studies focused on the common polymorphism, which was characterized by DNA sequencing as a G/T substitution at the first base of a recognition site for the transcription factor Sp1. Electrophoretic mobility shift assays (EMSA) confirmed that the polymorphism lay within an Sp1 binding site since the band shift corresponding to the Sp1-DNA complex was abolished by excess Sp1 oligonucleotide, but unaffected by AP1 or NFKB oligonucleotides (FIG. 1A). Further confirmation was provided by supershift assay which showed attenuation of the gel shift with an Sp1-specific monoclonal antibody and its restoration by the addition of excess Sp1 peptide (FIG. 1B).

A rapid PCR-based screening test for the polymorphism was devised (see methods) and the allele distribution studied in a cohort of 200 women. The allele frequencies were consistent with those predicted by the Hardy-Weinberg equation; "ss" homozygotes 9 (4.5%); "Ss" heterozygotes 71 (35.5%) and SS homozygotes 120 (60%). Analysis of these genotypes in relation to bone mass showed that adjusted BMD values at the lumbar spine were significantly reduced in both "Ss" and "ss" individuals when compared with the "SS" individuals with evidence of a gene-dose effect (FIG. 2).

The findings were similar when BMD was expressed as Z-score: (Spine Z score=−0.3+0.11 "SS"; vs −0.74+0.15 "Ss" vs −1.12+0.34 "ss"; $p<0.03$ ANOVA). Femoral neck BMD values followed a similar pattern but the difference between genotypes was not significant, possibly reflecting the greater importance of environmental factors in determining BMD at this site. In contrast, there was no significant difference between the genotypes in the following anthropomorphic and environmental variables: height (mean +sem; SS vs Ss vs ss respectively): 1.58+0.06 m vs 1.57+ 0.07 m vs 1.61+0.10 m; weight: 64.4+1.2 kg vs 61.5+1.4 vs 64.2+2.8; users of hormone replacement therapy: 11.5% vs 7.2% vs 12.5%; current smokers 15.9% vs 15.9% vs 12%; calcium intake: 446+38 mg vs 531+49 mg vs 563+157 mg.

Figure 3A:
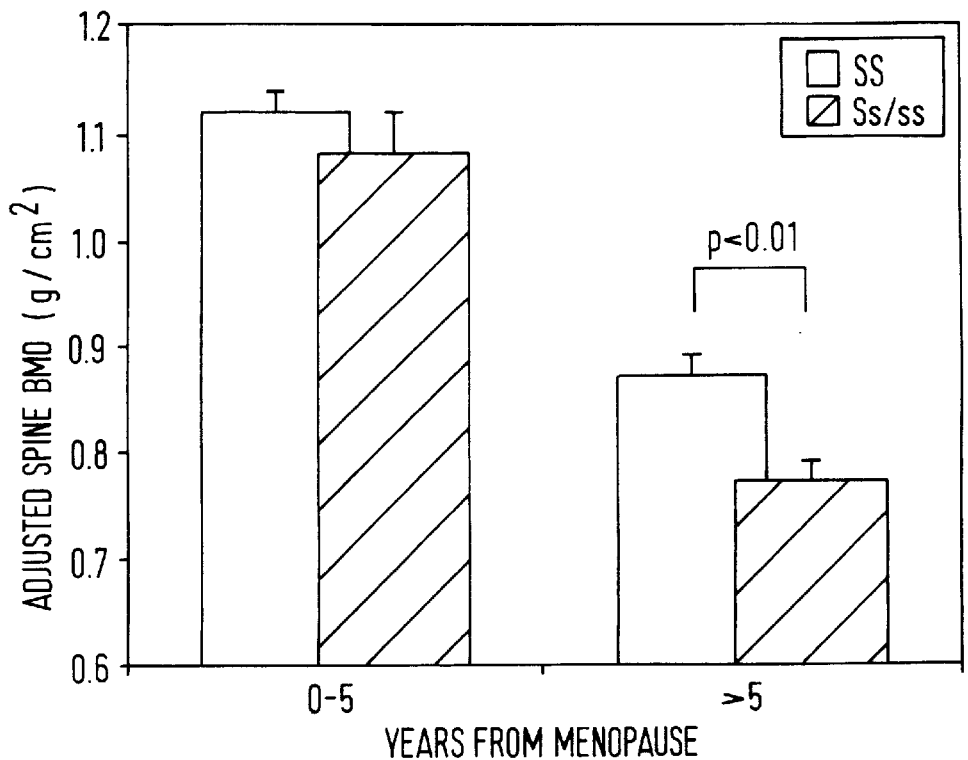
FIGS. 3A and 3B are bar graphs which show a COLIA1 Sp1 polymorphism and bone mineral density: effect of menopause.
Figure 3B:
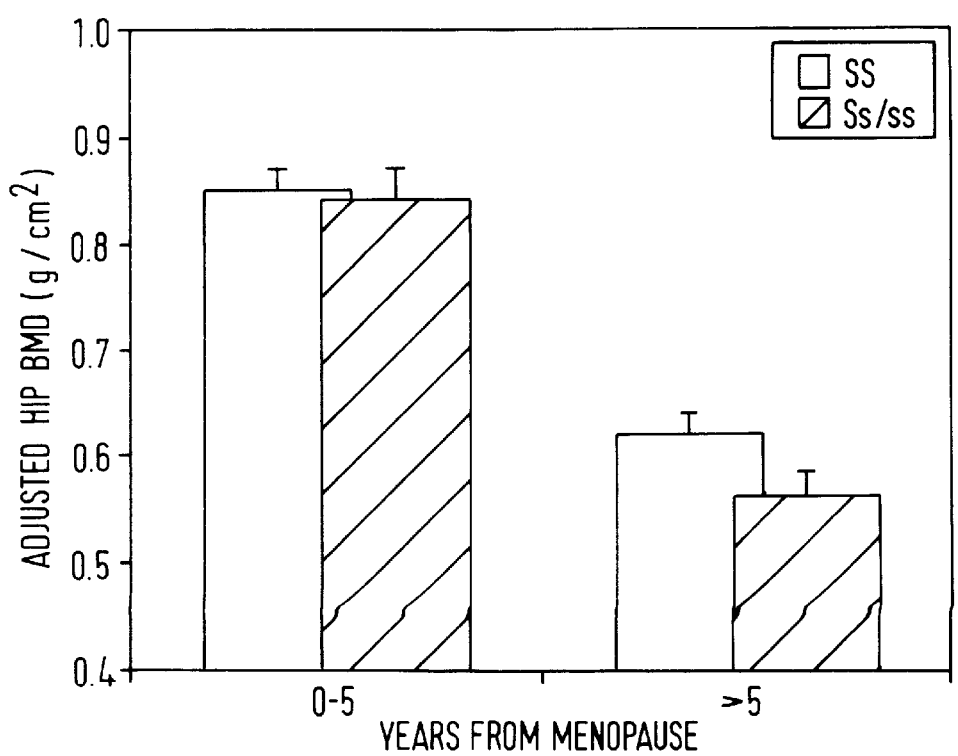
Figure 4:
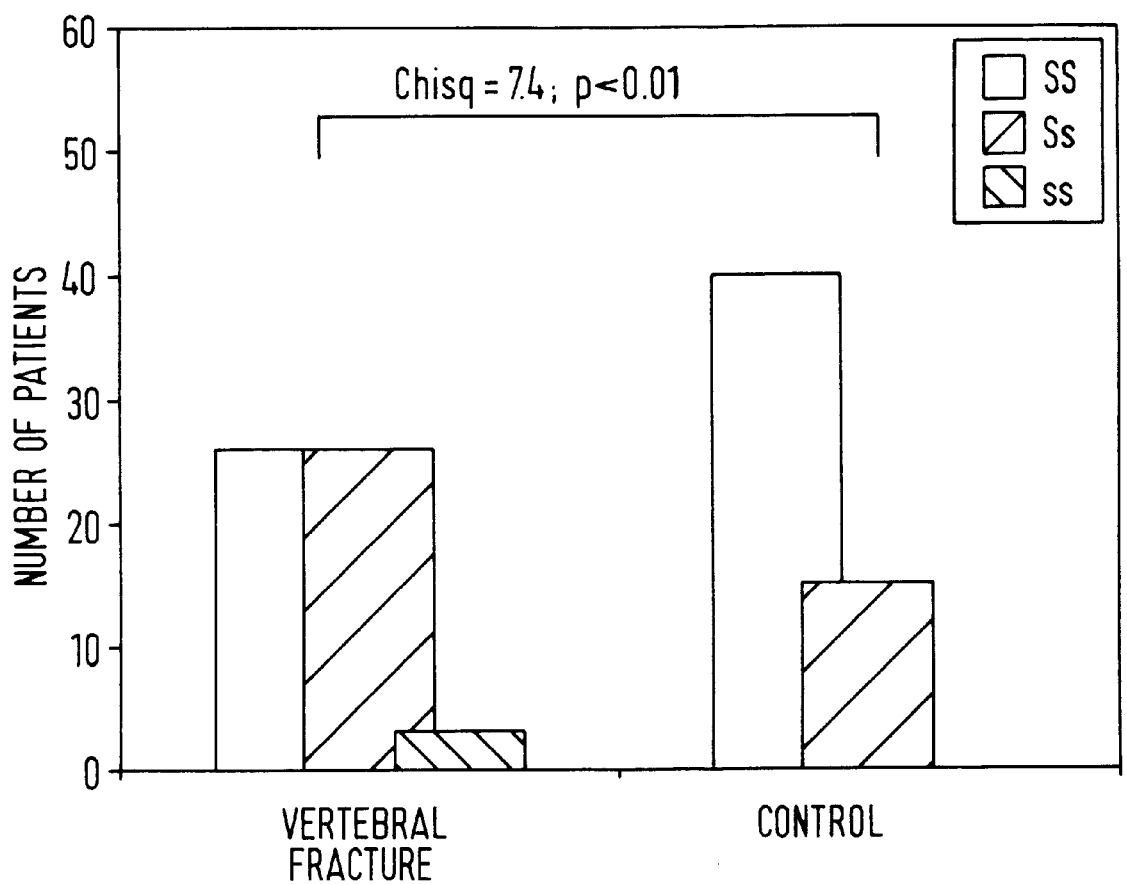
FIG. 4 is a bar graph which shows over-representation of COLIA1 "s" alleles in patients with osteoporotic vertebral fracture. Analysis of COLIA1 genotypes inpatients with osteoporotic vertebral fracture (n=55) and age-matched control subjects (n=55) showed significant over-representation of "s" alleles in the osteoporotic vertebral fracture group, equivalent to a relative risk for the presence of fracture of 2.97 95% CI=(1.63–9.56).

Since BMD in this age group reflects a balance between peak bone mass and rate of bone loss 1 we next analyzed the inter-relationship between COLIA1 alleles and menopausal status since this is an important determinant of BMD in women (FIG. 3). Here, adjusted BMD values were recalculated, excluding menopausal age as a co-variable. In the figure, data is pooled from the "Ss" and "ss" groups since BMD values were similar in these group and in view of the small number of "ss" homozygotes. This analysis showed that the difference in BMD between genotypes was accentuated in women 5 years or more post-menopause at both spine and hip. Although this was a cross-sectional study, the above observation raises the possibility that the "s" allele may act as a marker for increased post-menopausal bone loss rather than peak bone mass. In this regard, it is of interest in that osteogenesis imperfecta is also associated with an increased fracture rate after the menopause, presumably because the defect in collagen production accentuates the bone loss which normally occurs post-menopausally.

We next sought to determine if there was over representation of the "s" allele in patients with severe osteoporosis who had vertebral compression fractures. In this analysis, 55 patients with osteoporotic vertebral fractures were matched with 55 age and sex matched controls. In keeping with the BMD data, significant over representation of the "Ss" and "ss" genotypes was found in the vertebral fracture patients (54% vs 27%; Chisquare =7.42; df=1; $p<0.01$), equivalent to a relative risk for the presence of vertebral fracture of 2.97 (95% confidence interval 1.63–9.56).

Methods

Bone mineral density (BMD) was assessed by dual-energy X-ray absorptiometry as previously described (by Garton, M., Reid, I., Loveridge, N., Robins, S., Murchison, L., Beckett, G., and Reid, D. M., in Bone mineral density and metabolism in premenopausal women taking thyroxine, Clinical Endocrinology 41:747–755, 1995) and expressed as the T-score and the Z-score which relates actual bone density (g/square cm) to the normal population mean in locally derived young healthy individuals and in age matched controls, respectively. Adjusted BMD values (g/square cm) were also calculated by multiple linear regression analysis as previously described to correct for confounding factors which might influence BMD including age, menopausal age, height, weight, use of hormone replacement therapy, dietary calcium intake (by questionnaire) and smoking.

Results

Preliminary analysis showed that—in agreement with previous studies 18—the only variables which significantly influenced BMD were age, menopausal age and body weight. The adjusted BMD values shown are corrected for these variables, with the exception of the data in FIGS. 3A and 3B where menopausal age was excluded as a co-variable in the calculation. Polymorphisms in the promoter and intron 1 of COLIA1 were sought by PCR-SSCP on DNA extracted from whole blood using a kit (Nucleon; Scotlab, UK). Oligonucleotide primer sets (Oswell DNA services; University of Edinburgh, UK; sequences available from authors on request) were designed to yield 10 overlapping PCR fragments of 262–336 bp spanning the promoter (bases −751 to +39) and the first intron (bases +174 to +1805) of the human COLIA1 gene (FIGS. 1A and 1B). PCR (incorporating 2(Ci 32P dCTP in each reaction) was carried out under standard conditions using 0.1 ng DNA as template.

The products were resolved on native 5% polyacrylamide gels run at 20 degrees C. with 5% glycerol and detected by autoradiography for 2–3 days. In all cases, putative polymorphisms identified by SSCP were confirmed by direct sequencing (Applied Biosystems 373A DNA sequencer; Perkin Elmer, USA). Polymorphisms were subsequently detected by PCR mediated site-directed mutagenesis with a mismatched primer which introduced a restriction site for polymorphic alleles in amplified fragments. Electrophoretic mobility shift assays (EMSA) were performed using nuclear extracts prepared from MG63 cells (a human osteoblast-like cell line) using standard methods as previously described. A double stranded (32 P dATP -labeled oligonucleotide incorporating the polymorphic Sp1 binding site, was used as probe for EMSA with unlabelled double stranded oligonucleotides for Sp1, AP1 and NFkB in 100-fold molar excess as competitors. An Sp1-specific monoclonal antibody and Sp1 peptide (Santa-Cruz Biotechnology) were used at a final concentration of 0.5(g/tube in the supershift assays.

Conclusions

Thus, in a clinical study of 200 women, individuals homozygous or heterozygous for the T substitution (designated "Ss" and "ss" respectively) were found to have significantly lower spine BMD than homozygotes for the G substitution (designated "SS"), with evidence for a gene-dose effect of the "s" allele on bone mass. Further analysis showed that the difference in BMD between genotypes was accentuated in women more that 5 years post-menopause, raising the possibility that the "s" genotype may be associated with post-menopausal bone loss. Consistent with this hypothesis, the unfavorable "Ss" and "ss" genotypes were significantly over-represented in post-menopausal patients with severe osteoporosis and vertebral fractures, as compared with age and sex matched controls (54.7% vs 27.2%; (2=7.4; df=1; p<0.01), equivalent to a relative risk of 2.97 (95% confidence interval 1.63–9.56) for the presence of vertebral fracture.

EXAMPLE 2

Methods

185 Caucasian women (age range 44–64 years) were studied from an unselected sample of a large general practice in North-East London as part of the Chingford Population Study. Bone mineral density was measured at the lumbar spine (L1–L4) and femoral neck with dual energy X-ray absorptiometry (Hologic QDR-1000). Self-reported personal history of fracture was taken for the 10 year period preceding the study's onset (1978–88), and subsequently validated from radiographs and hospital records. Lateral spine X-rays were obtained on all women and thoracic and lumbar fractures were defined morphometrically using validated methods. Genotype analysis was performed using methods previously described, and alleles were coded as "S" (absence of Bal I restriction site) and "s" (presence of site). Urinary collagen cross-links (pyridinoline and deoxypyridinoline) were measured on fasting early morning urine samples in a subgroup of women using high pressure liquid chromatography.

Results

The genotype frequencies observed in the total group were in Hardy-Weinberg equilibrium and similar to those previously reported in the UK: SS 61.1% (n=113), Ss 36.2% (n=67), ss 2.7% (n=5). Given the small number of "ss" homozygotes, results from this group were pooled with the heterozygous genotype for subsequent analysis. Bone mineral density was significantly reduced at the lumbar spine in subjects with the "s" allele, mean difference (95% CI) 0.047 $g/cm^2$ (0.001, 0.093). A similar trend was also seen at the femoral neck, although this difference was not significant, mean difference (95% CI) 0.026 $g/cm^2$ (−0.013, 0.065). 55 validated fractures were observed in the total group, 28 vertebral and 27 appendicular. The frequency of the "Ss/ss" genotypes was significantly increased in fracture cases (49%) compared to controls (33%), with an odds ratio (95% CI) of 1.95 (1.01, 3.78). Examination of prevalent fractures at the two commonest sites of vertebra and wrist (Colles), showed a similar trend in the genotype distributions at each skeletal site although sample sizes were too small for significance to be demonstrated. Urinary collagen cross-link results were available on a subset of 82 subjects. Pyridinoline levels, but not deoxypyridinoline, were elevated in subjects with the "s" allele (p 0.05).

Conclusions

Our data show an association between COLIA1 polymorphism, low bone density and fracture.

EXAMPLE 3

Methods

The study group comprised a random age-stratified sample of 895 postmenopausal women aged 55–80 years from the Rotterdam study—a population-based cohort study of chronic diseases in the elderly. The polymorphism was typed by a polymerase chain reaction based assay and genotyping data was related to bone density, rate of bone loss and presence of vertebral fractures.

Results

Bone mineral density (BMD) was reduced in G/T heterozygotes (designated "Ss"), compared with G/G homozygotes ("SS") significant at the femoral neck (p=0.0009), Ward's triangle (p=0.02) and just above the level of significance in the spine (p=0.06). The rare T/T homozygotes ("ss") had lower BMD still consistent with a gene-dose effect on bone mass. A significant difference in the rate of fall in BMD with age was reflected by large genotype dependent differences in BMD from women in the eldest quartiles, suggesting that COLIA1 alleles may act as a marker for increased age-related bone loss. Longitudinal studies in a subgroup of 684 women supported this view in showing significantly faster rates of bone loss at Ward's triangle in Ss and ss genotypes over a 2 year period when compared with SS homozygotes (p=0.04). Finally, the low BMD-associated Ss and ss genotypes were significantly over-represented in 43 patients who had vertebral fractures compared with controls (Chisquare=4.1, p=0.04) corresponding to a relative risk of 1.9 (95 percent confidence interval, 1.0–3.5) for occurrence of fracture in carriers of the "a" allele.

Conclusions

These findings suggest that the COLIA1 Sp1 polymorphism is an important marker for reduced bone mass and osteoporotic fracture. They also indicate the allele associated with low BMD to determine age-related bone loss. A risk function for osteoporotic fracture including the COLIA1 Sp1 polymorphism can help in clinical practice to identify individuals at high risk of osteoporotic fracture for prophylactic therapy, before substantial bone loss has occurred.

Studies on the genetic basis of osteoporosis are important in identifying regulatory genes which might act as therapeutic targets, and in helping to develop methods of identifying individuals at risk of the disease. Our studies have revealed a strong association between bone mass and a common polymorphism which affects a regulatory motif in the transcriptional control region of the COLIA1 gene. We have furthermore demonstrated significant over-representation of the unfavorable "s" alleles in a cohort of patients with the clinically important condition of vertebral fracture. While the molecular mechanism by which this polymorphism affects bone density will require further study, our data identify COLIA1 as an important candidate gene for genetic regulation of bone mass and raise the possibility that genotyping at the Sp1 site may be of value in targeting individuals who are at risk of osteoporosis for early prophylactic therapy.

While the foregoing invention has been described in some detail for purposes of clarity and understanding, it will be appreciated by one skilled in the art from a reading of this disclosure that various changes in form and detail can be made without departing from the true scope of the invention and appended claims. All publications, patent applications and patents cited herein are incorporated by reference herein in their entirety.

---

What is claimed is:

1. A method of diagnosis of a predisposition to osteoporosis or an increased likelihood of having low bone mineral density comprising detecting the presence of a G to T polymorphism at position 1245 on a Col 1 alpha gene.

2. The method according to claim 1, wherein the polymorphism is detected using PCR primers which amplify a DNA segment comprising a nucleotide at position 1245 on a Col 1 alpha gene.

3. The method according to claim 2, wherein the PCR primers are SEQ ID NO: 2 and SEQ ID NO: 3.

4. An isolated DNA molecule comprising a collagen 1 alpha gene in which guanosine at position 1245 is substituted by thymidine.

5. An isolated DNA molecule comprising SEQ ID NO: 1.

6. A method of osteoporosis therapy comprising:
screening an individual for a genetic predisposition to osteoporosis; and
if such a predisposition is identified, treating that individual to prevent or reduce osteoporosis or to delay the onset of osteoporosis, wherein predisposition to osteoporosis is correlated with a G to T polymorphism at position 1245 of a Col 1 alpha gene.

7. A method according to claim 6 comprising treating the individual by hormone replacement therapy.

8. A pair of PCR primers which amplify a DNA segment of the Col 1 alpha gene, wherein the amplified DNA segment is up to 500 base pairs in length and nucleotide position 1245 of the Col 1 alpha gene is substantially towards the middle of the DNA segment.

9. A PCR primer, which is selected from the group consisting of SEQ ID NOs: 2 and 3.

10. A diagnostic kit comprising the pair of PCR primers according to claim 8.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 318 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

```
TAACTTCTGG ACTATTTGCG GACTTTTTGG TTCTTTGGCT AAAAGTGACC TGGAGGCATT      60

GGCTGGCTTT GGGGGACTGG GGATGGCCCC GAGAGCGGGC TTTTAAGATG TCTAGGTGCT     120

GGAGGTTAGG GTGTCTCCTA ATTTTGAGGT ACATTTCAAG TCTTGGGGGG GCCTCCCTTC     180

CAATCAGCCG CTCCCATTCT CCTAGCCCCG CCCCCGCCAC CCCACCTGCC CAGGGAATGT     240

GGGCGGGATG AGGGCTGGAC CTCCCTTCTC TCCTCCCTCG CCCTCCTCCT GTCTCTACCA     300

CGCAGCCACT CCCCACGA                                                   318
```

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

```
TAACTTCTGG ACTATTTGCG                                                  20
```

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear -continued (ii) MOLECULE TYPE: cDNA (xi) SEQUENCE DESCRIPTION: SEQ ID NO:3:

CCGGTCCTAC TCCCGACCTG                                           20